United States Patent [19]

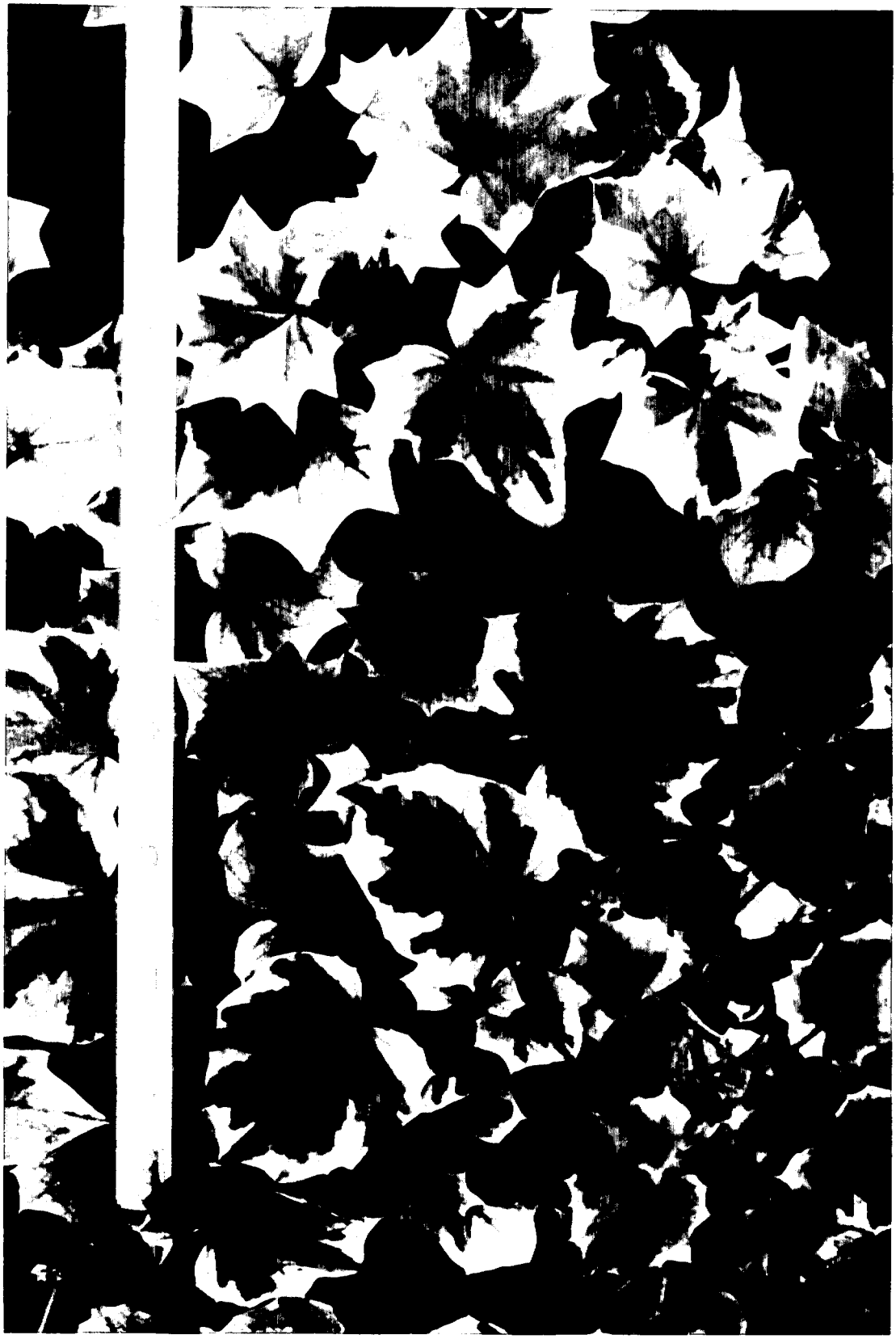

Morrison

[11] Patent Number: Plant 5,571

[45] Date of Patent: Oct. 8, 1985

[54] GERMAN IVY-PLANT 'MORRISON'S VARIEGATED'

[76] Inventor: Kenneth M. Morrison, P.O. Box 248, Forest Hill, La. 71430

[21] Appl. No.: 514,679

[22] Filed: Jul. 18, 1983

[51] Int. Cl.[4] ..... A01H 5/00

[52] U.S. Cl. ..... Plt./88

[58] Field of Search ..... Plt./88

[56] References Cited

U.S. PATENT DOCUMENTS

P.P. 4,818 1/1982 Flaist et al. ..... Plt./88

*Primary Examiner*—James R. Feyrer

[57] ABSTRACT

A new and distinct variety of the *Senecio mikanioides* family characterized by the well-defined variegation in the color of the leaves. Each plant has leaves that contain differing amounts of light and dark shades of green with a contrasting shade of cream color. The plant is unusually attractive when viewed with the normal green color of *Senecio mikanioides.*

1 Drawing Figure

BACKGROUND AND SUMMARY OF INVENTION

The present invention relates to a new and distinct variety of *Senecio mikanioides,* commonly known as the German Ivy plant, which is a bushy herbaceous plant, in time climbing, with glossy fresh green, ivy-shaped, lobed leaves rather soft-fleshly and producing fragrant yellow disk flowers. The new and distinct variety was discovered as a mutation of *Senecio mikanioides* and has been named the German Ivy Plant 'Morrison's Variegated'.

At the time of his discovery, the inventor was inspecting a group of hanging basket stock plants prior to removing cuttings for the purpose of propagation. During the inspection the inventor's attention was directed to a particular *Senecio mikanioides* plant. Upon closer inspection, the inventor discovered a single mutation growing from the center of the plant. The mutation consisted of a normal appearing stem approximately eight centimeters in length and bearing a number of variegated leaves which were quite different in appearance from the other leaves on the plant as well as different in appearance from the leaves which the inventor had seen on other *Senecio mikanioides* plants. In particular the variegated leaves were of the green color which is characteristic of the *Senecio mikanioides* variety with lighter shades of green radiating out in smaller, irregular areas and boardered on the edges by a cream color in an uneven pattern. With the exception of this mutation, the plant was typical of the *Senecio mikanioides* variety with green, ivy-shaped lobed leaves.

Upon the discovery of this new and distinct variety, the inventor immediately segregated it from the other plants, all of which were growing in a greenhouse that was located on the inventor's property in Forest Hill, La. After a period of observation, allowing for further growth, a tip cutting bearing a few variegated leaves was removed from the plant and inserted in a growing medium for the purpose of propagation. The result of this initial asexual reproduction of the mutation was successful and was followed by the removal of other cuttings as growth permitted. The inventor continued to use this method of asexual reproduction on the progeny of the original tip cutting. This resulted in numerous generations being successfully propagated all bearing variegated leaves with no entire reversions to the normal solid green color characteristic of the *Senecio mikanioides* variety. The inventor has observed, however the infrequent appearance of a single shoot with solid green leaves on a plant which otherwise is covered with variegated leaves. Asexual reproduction of these occasionally appearing shoots with green leaves results in plants with green leaves. These green leaf plants are twining in nature and often grow to a length of three meters at maturity. No detrimental affect has been observed on the variegation of leaves on the plants which occasionally produce a shoot with green leaves.

This new and distinct variety, named German Ivy Plant 'Morrison's Variegated' was not previously known to the inventor who, after numerous generations, has found this variegated variety to be stable and has observed that all reproductions run true to the original variegated mutation in all distinguishing characteristics.

DESCRIPTION OF DRAWING

The accompanying drawing serves, by photographic means, to illustrate the distinct colors of the variegated leaves of this new plant variety. The color photograph shows a top view of a potted arrangement of this present invention, Geman Ivy Plant 'Morrison's Variegated'.

BOTANICAL DESCRIPTION OF PLANT

The botanical details of this new and distinct variety of *Senecio mikanioides* as observed by the inventor under daylight conditions of specimen plants grown at his nursery in Forest Hill, La. with color definitions (except those in common color terms) referenced to Maerz and Paul Dictionary of Color (Second Edition) are as follows:

Name: German Ivy Plant 'Morrison's Variegated'.

Origin: A vegetative mutation on a plant of the *Senecio Mikanioides* variety.

Classification:

A. *Botanic.*—Compositae family.

B. *Commercial.*—Foliage plant.

C. *General.*—Herbaceous perennial.

Form: Semi erect, freely branching, trailing and cascading in time as a hanging basket or pot plant. Sprawling plant with creeping stems which root at the nodes, procumbent in habit as a ground cover.

Growth: Vigorous, self-branching, preferring cooler to moderate temperature for optimum growth.

Leaf:

A. *Shape.*—Ovate, acuminate tip, cordate base.

B. *Texture.*—Glabrous, thin, soft and fleshly.

C. *Margin.*—Pedately lobed.

D. *Arrangement.*—Alternate.

E. *Venation.*—Palmate.

F. *Attachment.*—Stalked.

G. *Size.*—4 cm to 5 cm wide, 4 cm to 5 cm long.

H. *Color.*—Variegated pattern of colors with leaf center predominately deep green, plate 22/J5, J8, blending into smaller areas of grayish green, plate 22/D1, H4, boardered by irregular areas of creamy white, plate 18/E1, G2, extending to the margins. When subjected to full sunlight for a prolonged period of time, the creamy white areas occasionally turn red, purple, plate 41/L7, L10.

Inflorescense: None produced.

I claim:

1. A new and distinct variety of *Senecio mikanioides* substantially as described and illustrated.

* * * * *